(12) United States Patent
Meathrel et al.

(10) Patent No.: US 7,727,466 B2
(45) Date of Patent: *Jun. 1, 2010

(54) DISINTEGRATABLE FILMS FOR DIAGNOSTIC DEVICES

(75) Inventors: William G. Meathrel, Glen Rock, PA (US); Nathan A. Meyer, Glen Rock, PA (US); Scott D. Barnhart, Glen Rock, PA (US); Cathy M. Moritz, Glen Rock, PA (US); Andrew P. Full, Glen Rock, PA (US); Susan R. Newsom, Oceanside, CA (US); Mary Robertson, Castletroy (IE)

(73) Assignee: Adhesives Research, Inc., Glen Rock, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/275,243

(22) Filed: Nov. 21, 2008

(65) Prior Publication Data

US 2009/0142850 A1 Jun. 4, 2009

Related U.S. Application Data

(63) Continuation of application No. 10/970,383, filed on Oct. 22, 2004, now Pat. No. 7,470,397.

(60) Provisional application No. 60/513,547, filed on Oct. 24, 2003.

(51) Int. Cl.
*G01N 33/548* (2006.01)
*G01N 33/532* (2006.01)

(52) U.S. Cl. .................. 422/56; 422/55; 422/50; 435/68.1; 435/4; 436/526; 436/518; 424/443; 424/435

(58) Field of Classification Search .............. 422/56; 424/443, 435; 435/68.1, 4; 436/526, 518
See application file for complete search history.

(56) References Cited

U.S. PATENT DOCUMENTS

| 4,029,757 A | 6/1977 | Mlodozeniec et al. |
| 4,029,758 A | 6/1977 | Mlodozeniec et al. |
| 4,031,200 A | 6/1977 | Reif |
| 4,136,145 A | 1/1979 | Fuchs et al. |
| 4,496,654 A | 1/1985 | Katz et al. |
| 4,661,162 A | 4/1987 | Kurihara et al. |
| 4,849,246 A | 7/1989 | Schmidt |

(Continued)

FOREIGN PATENT DOCUMENTS

EP  0653635 A  5/1995

(Continued)

*Primary Examiner*—Walter D Griffin
*Assistant Examiner*—Christine T Mui
(74) *Attorney, Agent, or Firm*—Dickstein Shapiro LLP

(57) ABSTRACT

The invention provides disintegratable film compositions for diagnostic test devices. The films are prepared with a combination of components that yield films of sufficient film strength and desired disintegration profiles. A disintegratable film according to the present invention contains a water soluble high molecular weight component, a water soluble low molecular weight component, and one or more reagents for use in a diagnostic device. Optionally, the films further contain a starch component, a glucose component, a plasticizer and/or a humectant, and/or a filler. The invention further provides a diagnostic testing device, which includes a film according to an embodiment of the invention, and methods of using such devices.

37 Claims, 1 Drawing Sheet

U.S. PATENT DOCUMENTS

| | | |
|---|---|---|
| RE33,093 E | 10/1989 | Schiraldi et al. |
| 4,876,092 A | 10/1989 | Mizobuchi et al. |
| 5,110,550 A | 5/1992 | Schlipfenbacher et al. |
| 5,346,701 A | 9/1994 | Heiber et al. |
| 5,369,015 A | 11/1994 | Yoshikawa et al. |
| 5,393,528 A | 2/1995 | Staab |
| 5,700,478 A | 12/1997 | Biegajski et al. |
| 5,712,172 A | 1/1998 | Huang et al. |
| 5,948,430 A | 9/1999 | Zerbe et al. |
| 6,007,999 A | 12/1999 | Clark |
| 6,120,802 A | 9/2000 | Breitenbach et al. |
| 6,120,856 A | 9/2000 | Liberti et al. |
| 6,177,096 B1 | 1/2001 | Zerbe et al. |
| 6,270,637 B1 | 8/2001 | Crismore et al. |
| 6,284,264 B1 | 9/2001 | Zerbe et al. |
| 6,403,298 B1 | 6/2002 | Lee et al. |
| 6,419,903 B1 | 7/2002 | Xu et al. |
| 6,645,731 B2 | 11/2003 | Terstappen et al. |
| 6,672,458 B2 | 1/2004 | Hansen et al. |
| 2003/0053962 A1 | 3/2003 | Zerbe et al. |
| 2003/0054039 A1 | 3/2003 | Zyck et al. |
| 2003/0099690 A1 | 5/2003 | Awamura et al. |
| 2005/0118217 A1* | 6/2005 | Barnhart et al. ............ 424/401 |
| 2005/0287682 A1 | 12/2005 | Lizzi et al. |
| 2008/0124381 A1 | 5/2008 | Barnhart et al. |

FOREIGN PATENT DOCUMENTS

| | | |
|---|---|---|
| WO | WO 88/09824 A | 12/1988 |
| WO | WO 99/41584 | 8/1999 |
| WO | WO 01/70194 A | 9/2001 |
| WO | WO 02/04570 A | 1/2002 |
| WO | WO 02/060980 A2 | 8/2002 |
| WO | WO 2004/087084 A1 | 10/2004 |
| WO | WO 2004/087089 A2 | 10/2004 |

* cited by examiner

DISINTEGRATABLE FILMS FOR DIAGNOSTIC DEVICES

CROSS REFERENCE TO OTHER APPLICATION

This patent application is a continuation of application Ser. No. 10/970,383, filed Oct. 22, 2004 now U.S. Pat. No. 7,470,397, which claims the benefit of U.S. provisional patent application No. 60/513,547, filed Oct. 24, 2003, and titled RAPIDLY DISSOLVING FILMS FOR DELIVERY OF PHARMACEUTICAL OR COSMETIC AGENTS, the entire disclosures of which are incorporated herein by reference.

FIELD OF THE INVENTION

The present invention is directed to disintegratable films, diagnostic devices containing such films, and methods for their use. More particularly, the present invention provides in one embodiment water soluble films containing soluble or dispersed reagents for use in diagnostic assay devices.

BACKGROUND OF THE INVENTION

In-vitro diagnostic devices are widely used. Useful diagnostic assay devices depend on biospecific affinity reactions for detecting, isolating, and/or separating cells, proteins, bacteria, viruses, nucleic acid sequences, and various other materials or compounds of interest. Many medical diagnostic tests require the detection, isolation, and/or measurement of specific compounds present in biological fluids such as blood, saliva, and urine.

Diagnostic tests can be conducted using a variety of devices, for example, electronic devices, biosensors, lateral flow devices, test strips, and test cards, among others. Often the necessary materials to conduct a test are provided in the form of a test kit, which may include a particular testing device. Some testing devices include the reagent or reagents necessary to perform a particular test. For other testing devices, the reagent(s) is obtained separately and used in connection with the testing device.

Substances which can be detected, measured, and/or isolated using an in-vitro diagnostic device include, for example, glucose; cholesterol; proteins, for example, various enzymes, such as amylase and creatine kinase; substances-of-abuse, for example, drugs regulated by law with respect to possession and use, such as methamphetamines; cells; bacteria; viruses; and nucleic acid sequences; among others. For example, pregnancy testing can be conducted using test strips to detect human chorionic gonadotropin (hCG). Such a test is described in U.S. Pat. Nos. 6,403,298 and 4,496,654. Also, diabetics and health care professionals use test strips for measuring blood glucose levels. U.S. Pat. No. 6,270,637 describes an electrochemical biosensor blood glucose test strip. Diagnostic testing, as described in U.S. Pat. No. 5,846,751, is used to detect helicobacter pylori bacterium in the human stomach to diagnose gastric disorders and duodenal ulcer disease. U.S. Pat. No. 6,645,731 describes the isolation of cancer cells from a biochemical matrix.

Lateral flow testing devices are commonly used. Typically, a lateral flow device includes a test strip, on which one or more reagents are present. To use the lateral flow testing device, a fluid sample is deposited onto the strip and migrates by capillary action along the strip where chemical reactions take place depending upon the presence or absence of the analyte in situ. Often, at least one reagent is included which manifests a detectable signal, for example a color change, in the presence of a minimal amount of the analyte of interest.

To fabricate test strips, aqueous solutions containing a reagent, for example, enzymes or antibodies, are localized on a supporting layer, which is a solid material, such as membrane support, an electrochemical sensor, cellulose or paper. The reagents are selected as necessary or helpful in detection of the analyte in question. Typically, the reagent is placed on the membrane by spraying, coating, or striping and then dried.

Other diagnostic testing devices require the use of various aqueous reagents. The reagents are typically applied by pipette directly to the sample to be tested.

Reagents can be expensive. Therefore, waste of reagents is undesirable. Conventional preparation techniques for test strips, such as spraying, coating or striping, can result in loss of reagent. Additionally, it is difficult to control the amount of reagent on the test strip using conventional techniques. Further, aqueous reagents can be cumbersome to handle. Some reagents are unstable in aqueous form and may require specialized storage, such as refrigeration.

Magnetic particles that have been functionalized with specific chemical reactive moieties also are known for use as reagents in immunoassays. In these assays, biochemical complexes are separated and isolated based on magnetic properties. U.S. Pat. No. 6,120,856 refers to the use of ferro fluids in diagnostic techniques including imunoassays, cell separation, toxicity testing, food testing, and environmental analysis. U.S. Pat. No. 6,672,458 describes the uses of functionalized paramagnetic particles for the separation and isolation of nucleic acid (DNA and RNA) from amplification techniques. Following amplification the cells are lysed and specific nucleic acid sequences are complexed to the functionalized paramagnetic particles. The paramagnetic particles with the bound nucleic acid are separated from the remaining solution using the magnetic properties of the complex.

However, it has been difficult to control the concentration of the magnetic particles due to static effects on the glass and plastic containers used in conventional diagnostic techniques. Plastic containers made from polystyrene and polypropylene are know to retain a static charge. The static charge on test tubes and other components causes problems in dispensing quantitative amounts of particles due to particle attraction to plastic and glass surfaces.

Accordingly, it would be desirable to provide reagent compositions and diagnostic devices that minimize or eliminate the above problems.

BRIEF SUMMARY OF THE INVENTION

The present invention provides disintegratable film reagent compositions prepared with a combination of components that yield films of sufficient film strength and desirable disintegration profiles for use in diagnostic testing. A disintegratable film according to the present invention contains a mixture of high molecular weight and low molecular weight water soluble components. The film also contains one or more reagents targeted to react with an analyte of interest or other reagents, such that the film can be used in a particular diagnostic test. Optionally, the films further contain a starch component, a glucose component, a plasticizer and/or a humectant. Also optionally, the film can include a filler, which is a dispersed phase or particle within the film to modify the disintegration profile of the film.

By "analyte" is meant the molecule or other substance in the sample to be detected. For example, an analyte, as used herein, may be a ligand, which is mono- or polyepitopic, antigenic or haptenic; it may be a single compound, such as chorionic gonadotropin, glucose, prostate specific antigen, or a plurality of compounds which share at least one common epitopic site; it may be an epitopic site of a viral, bacterial, or other pathogen; it may also be a receptor or an antibody, or any other chemical or biological substance, compound, or material suspected of being present in a sample of interest, including, but not limited to, a toxic substance, such as a pollutant, or a biological or chemical warfare agent.

Examples of "reagents" include, without limitation, specific antibodies or specific receptors, various iron oxide particles, magnetic, ferromagnetic or paramagnetic particles, and any substance that itself or in combination with other factors gives rise to a detectable signal or response when paired with an analyte of interest, for example, a pathogen (e.g., a bacteria, virus, or fungus); a protein (e.g., a growth factor, a lymphokine, a toxin, or a hormone); a cell surface (e.g., a cell adhesion molecule, a laminin, a fibronectin, an integrin, or a lectin); various drugs; metabolites; pesticides; or toxins.

A film according to an exemplary embodiment of the invention is preferably in the form of a monolayer. The monolayer can be cut to any desired size or shape for use in diagnostic testing applications.

The invention further provides a diagnostic testing device, which includes a film according to an embodiment of the invention, and methods for their use to detect the presence of an analyte of interest.

These and other advantages and features of the invention will be more readily understood from the following detailed description.

BRIEF DESCRIPTION OF THE DRAWINGS

The foregoing and other advantages and features of the invention will become more apparent from the detailed description of exemplary embodiments provided below with reference to the accompanying drawings in which.

DETAILED DESCRIPTION OF THE INVENTION

Figure 1:
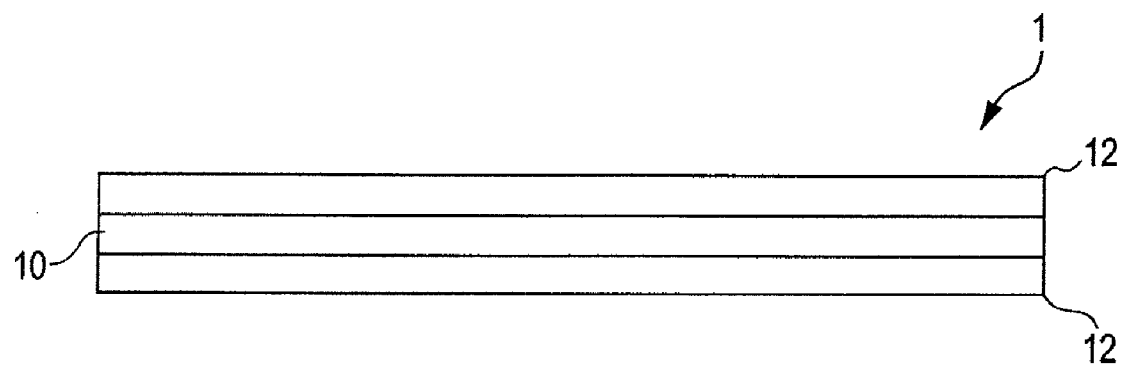
FIG. 1 illustrates a diagnostic testing device according to an exemplary embodiment of the invention.

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that various structural, biological, physical, and chemical changes may be made without departing from the spirit and scope of the present invention.

This invention incorporates test reagents and other chemical components into a dry disintegratable film. The film can be die cut and placed in a testing device or test strip used in various diagnostic techniques, including, but not limited to, immunoassays, cell separations, toxicity testing, food testing, environmental analysis, and emergency response test kits. A disintegratable film with a single reagent or multiple reagents can be used. Alternatively, multiple disintegratable films with single or multiple reagents may also be used in a diagnostic test device.

The disintegratable films according to the invention are comprised of a mixture of high molecular weight and low molecular weight water soluble components. In a preferred embodiment, the high molecular weight and low molecular weight water soluble components are water soluble polymers.

The film also includes one or more reagents, such that the film can be used in a particular diagnostic test. Optionally, the films may further include a starch component, a glucose component, a plasticizer and/or humectant; and/or other excipients in suitable amounts as described below, and which may be determined by one of ordinary skill in the art pursuant to the guidance provided by the examples and teachings herein. Preferably the films will have a thickness in the range of about 0.4 mil to about 10 mil, and more preferably within the range of about 0.4 mil to about 2 mil, although various other thicknesses are suitable as desired for particular applications as described in more detail below.

Each film can be characterized by its film strength and its disintegration profile (the speed at which the film will disintegrate in an aqueous media such as saliva). In known dissolvable films, surfactants have been used to affect the disintegration speed and decrease the time required for complete film disintegration. The present invention provides disintegratable film compositions that rapidly disintegrate upon application of a disintegration fluid, such as, but not limited to, blood, saliva, urine, and other aqueous biological and environmental fluids, and which, at the same time, have sufficient film strength without requiring the use of any surfactant. While a surfactant is optional in certain embodiments of the present invention, as described below, other embodiments are surfactant-free or substantially free of surfactants. The term "essentially free of surfactants" refers to trace amounts or higher levels of surfactants that are sufficiently low so as not to substantially increase the disintegration rate of the film composition following contact with a disintegrating fluid.

A disintegratable film containing one or more reagents can improve the stability of the reagents. Additionally, the reagents can be used more effectively and efficiently, since the film can be localized to a particular area within a testing device and can be handled easily as compared to an aqueous solution. Further, providing reagents in film form promotes efficient use and minimizes reagent wastage since a film can be divided into individual segments having a desired amount of reagent and the need for spraying, coating, or striping a reagent can thus be eliminated, if desired.

The high molecular weight and low molecular weight water soluble components of the disintegratable films according to the present invention may include a water-soluble polymer, including but not limited to, water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, xanthan gum, tragacantha, guar gum, acacia gum, arabic gum, carrageenan, polyacrylic acid, methylmethacrylate copolymer, carboxyvinyl copolymers, and various mixtures of the above and other known water-soluble polymers, cellulose derivatives, and/or gums, among others.

We have found that particularly beneficial properties of film strength and disintegration profile are obtained when the water soluble components include a combination of low molecular weight polymers (e.g., those less than about 5,000 to about 60,000 daltons) and high molecular weight polymers (e.g., those of about 60,000 to about 150,000 daltons, and to about 500,000 daltons or higher). For example, a combination of hydroxypropyl cellulose (e.g., Klucel, grade JF, Hercules Inc., Aqualon Division) and hydroxylpropyl methylcellulose (e.g., Methocel, grades E5, E50, E4M, and SG A16M by Dow Chemical) is suitable. These water soluble cellulose derivative polymers have molecular weights of about 140,000; 30,000; 90,000; 400,000; greater than about 100,000 daltons, respectively.

Additional water soluble polymers include polyvinyl pyrrolidone (PVP), such as Plasdone K-29/32 by ISP Corp., which has a molecular weight of about 58,000 daltons; polyvinyl alcohol-polyethylene glycol copolymer, such as Kollicoat IR by BASF Pharma, which has a molecular weight of about 49,000 daltons; and an acrylic polymer, sodium salt, such as Acrysol by Rohm and Haas, which is available in various grades having different molecular weights. Further, a water soluble polymer may serve the function of an additional optional component. For example, polyethylene oxide, such as, Polyox by Dow Chemical having a molecular weight of about 200,000 daltons, can serve as a high molecular weight water soluble polymer and a plasticizer, as discussed below.

The molecular weights of the water soluble polymers can be determined as described in Keary, "Characterization of METHOCEL Cellulose Ethers by Aqueous SEC with Multiple Detectors," Carbohydrate Polymers Vol. 45, pp. 293-303 (2001), which is incorporated herein by reference.

Various other polymers can be selected by one of ordinary skill in the art given the teachings herein, so long as the polymer is water soluble, and preferably includes a sufficient amount of a high molecular weight component to impart adequate film strength, and a sufficient amount of a low molecular weight component to facilitate the desired film property of rapid disintegration profile. Various concentrations of each polymer may be utilized. Such concentrations will typically be in the range of about 2% to about 35% based on the total weight of the dry film. In one embodiment, the concentration for the high molecular weight polymer is about 5% to 10% and the concentration of the low molecular weight polymer is about 5% to 10% of the dry film.

According to another exemplary embodiment of the invention, the water soluble low molecular weight component need not be a water soluble polymer. Instead, the low molecular weight component may be a low molecular weight monomer or a combination of various low molecular weight monomers. The low molecular weight component can also serve the function of an additional optional component. For example, the low molecular weight component can also serve as the reagent, a glucose component, a plasticizer, starch, thickener, buffer, stabilizer, and/or additive, and may include any of the specific compounds listed below or other suitable compounds, which are water soluble and have a molecular weight less than about 60,000 daltons. The low molecular weight component serves to promote rapid disintegration, but is present in an amount such that film strength is adequate for processing and dispensing. Various concentrations of the low molecular weight component can be utilized. Such concentrations will typically be in the range of about 2% to about 80% or more based on the total weight of the dry film. In one embodiment, the concentration for the high molecular weight polymer is about 5% to 10% and the concentration of the low molecular weight component is about 30% to 80% of the dry film.

The amounts of high and low molecular weight components can be adjusted to achieve a desired disintegration profile for the film. When slower disintegration is desired, the concentration of the high molecular weight component can be increased relative to the concentration of the low molecular weight component. When faster disintegration is desired, the concentration of the low molecular weight component can be increased relative to the concentration of the high molecular weight component. Additionally, the thickness of the film can be adjusted to achieve a desired disintegration profile. To increase the disintegration time, the film thickness is increased. Adequate film strength should be maintained to allow for processing of the film.

In addition to a desired disintegration time, the films according to the invention have adequate strength for processing, packaging, and administration without physical failure (e.g., breakage, fracture, or otherwise) during processing and normal handling prior to packaging and use in a desired diagnostic device or testing application. The film strength, specifically, film resilience, springiness and burst strength, can be determined using the TA.XT2i Texture Analyzer by Texture Technologies Corp. and the ASTM D3763 "High Speed Puncture Properties of Plastics Using Load and Displacement Sensors" test method. These properties of film strength and rapid disintegration are the result of the unique combination of the components described herein. By "rapid" disintegration, we mean that the reagent is released from the film matrix in less than about minute. Disintegration times can be determined using the test provided by (USP) 24, Disintegration <701>. See United States Pharmacopoeia, 24th ed., Ch. 701, p. 1941 (2000), which is incorporated herein by reference.

The optional glucose component of thin films according to the invention can be added to promote disintegration of the film upon contact with a disintegrating fluid. Preferably, the glucose component comprises a water soluble polymer or mixture of polymers having D-glucose units. The dextrose equivalent (DE) of the glucose component is preferably within the range of about 10 to about 25, or about 15 to about 20, although various other DE ranges can also be used. The glucose component can be prepared, for example, by the partial hydrolysis of starch to yield D-glucose polymer mixtures. Suitable commercially available glucose components include, for example, maltodextrin, corn syrup solids, sucrose, and dextrose. Maltodextrin having a DE of about 16.5 to 19.5, such as that commercially available from Grain Processing Corp. (GPC) under the trade name "Maltrin M180," is particularly suitable, although various other glucose containing polymers and mixtures can be utilized, including, for example, other grades of "Maltrin," "Lycatab DH" (Roquette Freres), and "Star-Dri" (A. E. Staley). Suitable concentrations as a weight percentage of the dry film composition will typically be in the range of about 2% to 20%, or about 3% to about 15%, although other concentrations also may be used depending on the selection of other components and the desired film properties.

The optional starch component of films according to the present invention can be added to promote disintegration of the film upon contact with a disintegrating fluid. The starch component can also serve to increase the solids content of the film and add bulk. Preferably, the starch component is a water soluble polysaccharide composition containing amylose and/or amylopectin. Such compositions may be prepared by, for example, modifying natural starches, such as corn, wheat, rice, potato, or tapioca starch, to provide cold water soluble instant starches. Various water soluble compositions of amylose and/or amylopectin polysaccharides can be used. Typically, these can be made by heating a natural starch with steam to modify the natural starch product so that it is cold water soluble.

The instant starch commercially available from GPC, Muscatine IA, as "Instant Pure Cote B792," (IPC B792) is an exemplary starch component for purposes of the present invention. Other suitable commercially available instant starches include "Polartex Instant 12640," available from Cargill, Inc., and various others may also be utilized. The starch component will typically have an amylose to amylopectin ratio in the range, for example, of about 0 to about 2.5. The starch can be incorporated in the wet film composition in any suitable amount, including, but not limited to, about 2% to 50%, or about 3% to about 35% by weight based on the dry film.

The disintegratable film compositions of the present invention may also optionally contain a plasticizer or humectant, for example, polyalcohols, sorbitan esters, and citric acid esters, to increase the flexibility of the films. The plasticizers can be added directly to the formulation during manufacture. Suitable compounds include polyethylene glycol (PEG), such as Lutrol E 400, by BASF Pharma; polyethylene oxide, such as Polyox by Dow; polyoxamers, such as Lutrol F by BASF Pharma; polyvinyl alcohol; polyvinyl methyl ether, such as Lutanol by BASF; or mixtures of such polymers; triacetin; glycerin; mannitol; xylitol; and various other polyalcohols and other compounds having plasticizer and/or humectant properties can be satisfactorily employed. Sorbitol and PEG 400 are particularly suitable; although compounds having a higher molecular weight (e.g., Polyox N80) than PEG 400 can be desirable for certain applications, since they are typically less volatile than sorbitol and PEG 400. The optional plasticizer and/or humectant may be present in any suitable range, including, for example about 3% to 30%, 10% to 20%, or 15% to 18% by weight of the dry film.

Further, thickeners, buffers, stabilizers, additives and/or other components can be added to the film formulations according to the invention to provide a film having desired properties. For example, in some cases it may be desirable to use films that exhibit different disintegration times or disintegrate under different conditions, such as at elevated pH. In such a case, an additional component can be added to the film composition. For example, to configure the film to disintegrate based in part on the pH level of the solublilizing fluid a thickener, such as Carbopol 940 by Noveon, Inc. can be added.

As noted above, according to one exemplary embodiment, the films according to the invention can contain a filler, which is a dispersed phase or particle. The filler can add bulk to the film; increase the solids portion of the film, which can aid in coating; and/or can cause the films to disintegrate faster upon contact with the disintegrating fluid, i.e., biological sample or other aqueous material suspected of containing an analyte of interest.

The filler can be a reagent or an optional additional component. The filler can be an optional non-active component. Examples of such components include titanium oxide and microcrystalline cellulose, which is available under the name Avicel, among others. Air or other gasses can also be used as a filler according to the invention. When air is employed as the filler, a surfactant (e.g., sodium lauryl sulfate (SLS), available under the name Stepanol, Polysorbate 80, or Pluracare F87 Pril NF) may be included in the film formulation. The surfactant does not itself serve to significantly increase the rate of disintegration of the films. Instead, the surfactant aids in the processing and formation of the film. Specifically, the surfactant stabilizes the gaseous bubbles as a dispersed phase within a solution to allow the solution to be processed, as described in more detail below, to form the film containing the gas or air as a dispersed phase filler.

The particular components for a film can be chosen as desired and as are compatible with a particular testing scheme. For example, the optional glucose component would typically be omitted from a film to be employed in a blood glucose testing device.

The film compositions according to the invention may be prepared by several methods, including, but not limited to, adding the combination of high and low molecular weight water soluble components, the optional starch, and optional glucose ingredients to a solvent that is capable of dissolving them, such as water or ethanol or a mixture of ethanol and water. Upon forming a homogeneous solution, the reagent and any of the other optional components, such as plasticizers, colorants, and/or other components may be blended into the reagent-containing polymer solution. Alternatively, all of the film components may be added and concurrently blended to form a solution or dispersion. Also, a dry blend can be compounded by a V-blender. The dry blend can be subsequently used to form a solution or dispersion. Additionally, the dry blend can be subjected to a melt extrusion process to form a film upon cooling. It should be understood that no particular sequence of steps is required, except as needed to effectively prepare a desired film composition. For example, if a particular sequence yields an undesirable precipitate, an alternative sequence may be used.

The reagent may be soluble in the solution or it may be suspended or dispersed in the solution. Any reagent or combination of reagents suitable for a particular diagnostic test can be used. Suitable reagents for particular diagnostic tests are known in the art and continue to be discovered or created. Examples of reagents include, but are not limited to, proteins, enzymes, antibodies, substances that display magnetic properties, iron oxide, and other compounds or combinations of compounds which display a physical change, such as a color change upon exposure to a particular substance or magnetic field.

The reagent-containing solution or dispersion may be further processed into a film by any one of many casting, drawing, or extruding techniques. For example, the solution or dispersion may be sprayed onto a support such as a release-treated belt. Alternatively, for example, the solution or dispersion may be roll coated onto a release treated paper or film substrate.

After coating of the solution or dispersion onto a support surface, the solvent may be removed by radiant energy (such as infra-red), heat, convection, vacuum, or any combination of these to yield a dry film containing one or more reagents. The resulting dry film can be wound up into a roll for storage prior to further processing into individual films for specific diagnostic devices. Whether stored for future processing or immediately following removal of the solvent, the resulting film can be removed from the support surface and subsequently processed for various end use applications.

The dry film can be further processed by any suitable technique, including, for example, by die-cutting or cutting across the width of a singular narrow roll to prepare segments of any desired geometric size or shape. The segments may be subsequently packaged and/or further processed and incorporated into a testing device. When a film is incorporated into a device in place of a test strip manufactured by conventional processes, the efficiency of the manufacturing process can be improved. Specifically, the continuing processing of rolls of reagent containing film, die cutting, and reagent placement can be less wasteful than conventional spraying, coating, or striping processes. Additional ingredients can be applied to the dried film by, for example, printing, spraying, dusting, or vapor adsorption processes, among others.

A testing device 1 including a disintegratable film 10 according to an exemplary embodiment of the invention is shown in FIG. 1. The disintegratable film 10 is used to create a fluid channel upon application of a disintegrating fluid (not shown), such as blood, saliva, or urine. The film 10 can be die cut from a roll to create a fluidic pathway pattern. The film pattern can be sandwiched between adjacent layers such as adhesive coatings 12. The adhesive coatings 12, can be, for example, Adhesives Research, Inc.'s ARcare 8890, ARcare 7840, or ARcare 7841, which are double faced adhesive constructions used in forming fluidic channels for testing devices. Although the testing device 1 includes a single disintegratable film 10 according to the invention, the testing device 1 could instead include more than one film 10. Alternatively, a fluid channel can be created using, for example, a screen printed or jet printed high coat weight ink.

Figure 2:
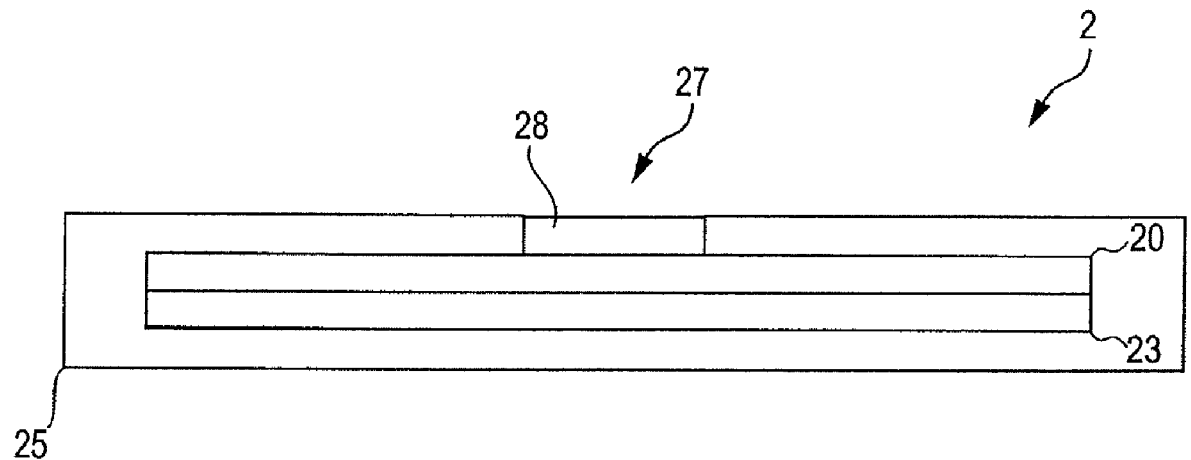
FIG. 2 is a block diagram of a testing device according to another exemplary embodiment of the invention.

According to another embodiment of the invention, a disintegratable film 20 can be used to protect and isolate a reactive layer 23 or reagent in a diagnostic testing device 2, as shown in FIG. 2. The reactive layer 23 containing one or more reagents and the film 20 are within a fluid channel 27 and are supported by a support structure 25. The fluid channel 27 may or may not be covered by a cover 28. The cover 28 is preferably a transparent cover, and can be, for example an adhesive material heat bonded to the support structure 25.

According to the embodiment shown in FIG. 2, the reactive layer 23 is a disintegratable film according to the invention. Instead, the reactive layer 23 can be a conventional reactive layer. The reactive layer 23 is isolated by the film 20 until the film is disintegrated by a disintegrating fluid (not shown). In such case, the film 20 need not include a reagent. The film 20 is configured to act as a barrier to the reactive layer 23. Upon application of a disintegrating fluid, such as saliva, blood or urine, to the fluid channel 27, the barrier film 20 disintegrates allowing an analyte (not shown) contained in the fluid to encounter the reactive layer 23. Thereby, the interaction between reactive components in the testing device 2 can be controlled by choice of disintegration time and/or conditions (e.g., pH, temperature, ionic strength, among others).

The devices of FIGS. 1 and 2 are exemplary only, and the films according to the invention can be included in other testing devices, such as electronic devices, biosensors, various lateral flow devices, and test cards, among others. The films may also be packaged and provided as part of a test kit.

The following illustrative examples provide a number of specific formulations within the scope of the present invention. These examples are by way of illustration only and are not intended to be limiting in any way. Various alternative components, concentrations, and optional excipients (plasticizers, humectants, fillers, preservatives, etc.) may be utilized given the teachings herein to yield thin films of suitable film strength and disintegration profile.

Specific embodiments of the invention are illustrated in the examples below. The examples are not meant to be limiting. Accordingly, additional formulations according to the invention can be made according to the teachings herein. The concentrations of the excipients are expressed as approximate parts per 100.

Examples 1-3 illustrate films suitable for use in pregnancy testing in humans. As is known in the art, pregnancy testing is conducted by detecting human chorionic gonadotropin (hCG) in, for example, a urine or blood sample. Such tests are described in U.S. Pat. Nos. 6,403,298; 5,712,172; and 4,496,654; which are incorporated herein by reference. The reagents listed in examples 1-3, specifically, the organic salt, organic base, inorganic base, organic acid, and protein, can be those known in the art which are suitable to permit the detection of hCG in a sample, such as those disclosed in U.S. Pat. Nos. 4,496,654 and 5,712,172. Further, each of the reagents may be a combination of individual ingredients. For example, the protein may be a combination of antibodies.

Example 1 is a composition for films suitable for use in an hCG test strip according to an exemplary embodiment of the invention. The films of example 1 can be used together in a single test strip. The first film contains two reagents, an organic acid and an inorganic base, and the second film contains two reagents, an organic salt and an organic amine. The films each include a common base solution.

Base Solution for Examples 1 and 2

| Component | Parts |
| --- | --- |
| Deionized water | 81.8 |
| Methocel E50 | 2.3 |
| Methocel E5 | 3.0 |
| Maltrin M180 | 2.3 |
| IPC B792 | 2.9 |
| Triacetin | 2.6 |
| Polysorbate 80 | 3.4 |
| Ethanol | 1.7 |

EXAMPLE 1

Film 1: Buffer Component

| Component | Parts |
| --- | --- |
| Deionized water | 15.6 |
| Organic acid | 2.84 |
| Inorganic base | 11.1 |
| Base solution | 70.4 |

Film 2: Protein Component

| Component | Parts |
| --- | --- |
| Organic salt | 3.8 |
| Organic amine | 6.1 |
| Base solution | 90.1 |

Examples 2 and 3 illustrate the composition for a single film suitable for use in an hCG test strip according to additional exemplary embodiments of the invention. The films of examples 2 and 3 each include four reagents.

EXAMPLE 2

| Component | Parts |
| --- | --- |
| Deionized water | 18.4 |
| Organic acid | 0.66 |
| Organic base | 2.48 |
| Organic salt | 1.83 |
| Organic amine | 1.73 |
| Base solution | 74.9 |

EXAMPLE 3

| Component | Parts |
| --- | --- |
| Kollicoat IR | 58.0 |
| Polymer | 1.0 |
| Organic base | 26.0 |
| Organic salt | 10.0 |
| Protein | 2.0 |
| Acrysol 6038a | 4.0 |

Examples 4 and 5 illustrate film compositions including iron oxide according to additional exemplary embodiments of the invention.

EXAMPLE 4

| Component | Parts |
| --- | --- |
| Deionized water | 59.0 |
| Methocel E50 | 3.2 |
| Methocel E5 | 4.5 |
| Maltrin M180 | 3.5 |
| Pure-Cote | 3.5 |
| Triacetin | 3.7 |
| Polysorbate 80 | 4.9 |
| Ethanol | 2.5 |
| Iron oxide | 15.1 |

Methocel E5, Methocel E50, Maltrin M180 and Pure-Cote are added to boiling water with constant stirring. The mixture is cooled to about room temperature under agitation to allow the components to solubilize. The iron oxide is mixed with triacetin, polysorbate 80 and ethanol until the iron oxide is wetted out. The aqueous solution is added to the iron oxide mixture and stirred to form a homogeneous mixture. The mixture is deairated prior to coating onto a release liner. The coating is dried at about 120 degrees C. for about 5 minutes.

EXAMPLE 5

| Component | Parts |
| --- | --- |
| Deionized water | 57.2 |
| Methocel E50 | 8.6 |
| Glycerin | 4.3 |
| Iron oxide | 29.9 |

Examples 6-9 are prophetic examples, which illustrate exemplary film formulations according to the invention. The reagent component(s) is not listed as being a specific reagent. Any suitable reagent can be used. The films of examples 6-9 contain substantially no surfactants.

EXAMPLE 6

| | Parts |
| --- | --- |
| Methocel E5 | 3.84 |
| Methocel E50 | 10.52 |
| Klucel JF | 1.70 |
| Maltrin M180 | 2.27 |
| IPC B792 | 2.27 |
| Reagent 1 | 19.82 |
| Reagent 2 | 39.97 |
| Sucralose | 2.00 |
| Sorbitol | 8.28 |
| FD&C Red #40 | 0.08 |
| PEG 400 | 9.25 |

EXAMPLE 7

| | Parts |
| --- | --- |
| Methocel E5 Prem LV | 6.14164 |
| Methocel E50 FG | 4.34101 |
| Klucel JF | 2.71067 |
| Maltrin M180 | 3.70464 |
| IPC B792 | 3.70193 |
| Sorbitol | 18.5 |
| Sucralose | 2 |
| FD&C Red #40 | 0.15 |
| Reagent 1 | 40.0001 |
| Reagent 2 | 18.75 |

EXAMPLE 8

| | Parts |
| --- | --- |
| Methocel E5 | 7.60 |
| Methocel E50 | 5.32 |
| Klucel JF | 3.31 |
| Maltrin M180 | 4.63 |
| IPC B792 | 4.63 |
| Reagent 1 | 39.55 |
| Reagent 2 | 15.58 |
| Sucralose | 2.65 |
| Sorbitol | 16.59 |
| FD&C Red #40 | 0.15 |

EXAMPLE 9

| | Parts |
| --- | --- |
| Methocel E5 | 9.96 |
| Klucel JF | 7.12 |
| Maltodextrin | 14.31 |
| IPC B792 | 14.31 |
| Sucralose | 2.38 |
| Reagent | 37.00 |
| Sorbitol | 14.93 |

The examples above illustrate disintegratable film formulations that disintegrate in biological fluids, such as saliva, urine or blood. The above examples are not meant to be limiting. Accordingly, many additional film compositions are possible within the scope of the invention, as defined by the appended claims and equivalents thereof.

The above description is only illustrative of preferred embodiments which achieve the objects, features and advantages of the present invention. It is not intended that the present invention be limited to the illustrated embodiments. Any modification of the present invention which comes with the spirit and scope of the following claims is considered part of the present invention.

What is claimed as new and desired to be protected by Letters Patent of the United States is:

1. A disintegratable film for a diagnostic device capable of detecting the presence of an analyte of interest in an aqueous fluid sample, comprising:
    a first water soluble polymer having a molecular weight less than about 49,000 daltons;

a second water soluble polymer having a molecular weight greater than about 60,000 daltons; and at least one reagent capable of permitting detection of an analyte of interest in an aqueous fluid sample, wherein the film is in the form of a monolayer of a thickness sufficient to disintegrate upon contact with the aqueous fluid applied to the diagnostic device to release the reagent.

2. The film of claim 1, wherein the concentration of the first and second water soluble polymers present in the film is about 2% to 80% of the weight of the film.

3. The film of claim 1, wherein the second water soluble polymer has a molecular weight of greater than about 60,000 to about 500,000 daltons.

4. The film of claim 1, wherein at least one of the first and second water soluble polymers comprises hydroxypropyl cellulose.

5. The film of claim 1, wherein at least one of the first and second water soluble polymers comprises hydroxypropyl methylcellulose.

6. The film of claim 1, wherein the first and second water soluble polymers comprise hydroxypropyl methylcellulose.

7. The film of claim 1, wherein the at least one reagent comprises iron oxide.

8. The film of claim 1, wherein the film disintegrates in less than about 60 seconds after contact with an aqueous fluid.

9. The film of claim 1, wherein the film has a thickness of about 0.4 to about 10 mil.

10. The film of claim 1, wherein the film is part of a multilayer device.

11. The film of claim 1, wherein the film is essentially free of surfactants.

12. The film of claim 1, further comprising a third water soluble polymer.

13. The film of claim 1, wherein the second water soluble polymer comprises cellulose derivative polymers having a molecular weight in the range of about 60,000 to about 500,000 daltons, and wherein the first water soluble polymer comprises cellulose derivative polymers having a molecular weight of about 5,000 to about 60,000 daltons.

14. The film of claim 1, wherein the concentration of the first water soluble polymer is about 2% to 10% of the weight of the film and wherein the concentration of the second water soluble polymer is about 2% to 10% of the weight of the film.

15. The film of claim 1, further comprising a starch component.

16. The film of claim 15, wherein the concentration of the starch component is about 2% to 50% of the weight of the film.

17. The film of claim 1, further comprising a glucose component.

18. The film of claim 17, wherein the concentration of the glucose component is about 2% to 20% of the weight of the film.

19. The film of claim 1, further comprising a plasticizer and/or humectant.

20. The film of claim 19, wherein the concentration of the plasticizer and/or humectant is about 3% to 30% of the weight of the film.

21. The film of claim 1, further comprising a filler.

22. A method of performing a diagnostic test using the film of claim 1 wherein the film is placed in contact with a sample for a sufficient period of time to disintegrate the film and release the at least one reagent.

23. A disintegratable film for a diagnostic device capable of detecting the presence of an analyte of interest in an aqueous fluid sample, comprising:

a first water soluble polymer having a molecular weight of about 30,000 daltons or less;

a second water soluble polymer having a molecular weight of about 90,000 daltons or greater; and at least one reagent capable of permitting detection of an analyte of interest in an aqueous fluid sample, wherein the film is in the form of a monolayer of a thickness sufficient to disintegrate upon contact with the aqueous fluid applied to the diagnostic device to release the reagent.

24. The film of claim 23, wherein the first water soluble polymer comprises a first hydroxypropyl methylcellulose polymer and wherein the second water soluble polymer comprises a second hydroxypropyl methylcellulose polymer.

25. The film of claim 24, wherein the at least one reagent comprises iron oxide.

26. The film of claim 24, wherein the first hydroxypropyl methylcellulsoe polymer comprises about 2 percent to about 10 percent of the weight of the dry film.

27. The film of claim 26, wherein the second hydroxypropyl methylcellulsoe polymer comprises about 10 percent to about 35 percent of the weight of the dry film.

28. The film of claim 23, further comprising a surfactant.

29. A testing device comprising:

a support structure; and at least one disintegratable film supported by the support structure, the disintegratable film comprising:

a first water soluble polymer having a molecular weight less than about 49,000 daltons;

a second water soluble polymer having a molecular weight greater than about 60,000 daltons; and at least one reagent capable of permitting detection of an analyte of interest in an aqueous fluid sample, wherein the film is in the form of a monolayer of a thickness sufficient to disintegrate upon contact with the aqueous fluid applied to the diagnostic device to release the reagent.

30. The testing device of claim 29 wherein the at least one reagent comprises iron oxide.

31. The testing device of claim 29 further comprising a plurality of films.

32. The testing device of claim 29 wherein the at least one reagent is within the film.

33. The testing device of claim 29 wherein the film is configured within the device to isolate the at least one reagent.

34. The testing device of claim 29 wherein the film is configured to disintegrate based in part on the pH of the disintegrating fluid.

35. The testing device of claim 29, wherein the device is a lateral flow device.

36. The testing device of claim 29, wherein the support structure is an adhesive coating.

37. A method of performing a diagnostic test using the testing device of claim 30 wherein a sample is placed in contact with the at least one disintegratable film for a sufficient period of time to disintegrate and release the one or more reagents.

* * * * *